United States Patent [19]

Taguchi et al.

[11] Patent Number: 5,700,931

[45] Date of Patent: Dec. 23, 1997

[54] 7-SUBSTITUTED-2-OXA[3.2.0]HEPTAN-6-ONE COMPOUND AND METHOD FOR THE PREPARATION THEREOF

[75] Inventors: Yoichi Taguchi; Akihiro Oishi; Isao Shibuya; Tohru Tsuchiya, all of Tsukuba, Japan

[73] Assignee: Japan as represented by Director General of Agency of Industrial Science and Technology, Japan

[21] Appl. No.: 654,521

[22] Filed: May 29, 1996

Related U.S. Application Data

[62] Division of Ser. No. 396,778, Mar. 1, 1995, Pat. No. 5,550,230.

[30] Foreign Application Priority Data

Mar. 8, 1994 [JP] Japan ........................... 6-65500

[51] Int. Cl.$^6$ .................. C07D 491/048; A61K 31/395
[52] U.S. Cl. .................................................. 540/203
[58] Field of Search ................................. 540/203

[56] References Cited

FOREIGN PATENT DOCUMENTS

| | | |
|---|---|---|
| 0509821A1 | 10/1992 | European Pat. Off. . |
| 0516486A3 | 12/1992 | European Pat. Off. . |
| 0523904A1 | 1/1993 | European Pat. Off. . |
| 0546742A1 | 6/1993 | European Pat. Off. . |
| 0564129A3 | 10/1993 | European Pat. Off. . |
| 1277258 | 3/1963 | Germany . |
| 63-45250 | 2/1988 | Japan . |

OTHER PUBLICATIONS

*Patent Abstracts of Japan*, vol. 11, No. 63 (C–406) [2510] (Feb. 1987) (abstract of JP–A–61–225179.
Lattrell, Liebigs Ann. Chem. 722, 132–141 (1969).

*Primary Examiner*—Mark L. Berch
*Attorney, Agent, or Firm*—Wenderoth, Lind & Ponack

[57] ABSTRACT

Disclosed is a novel β-lactam compound, a 7-substituted-2-oxa-7-azabicyclo[3.2.0]heptan-6-one represented by the general formula

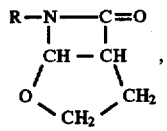

in which R is an alkyl, cycloalkyl, aryl, halogen-substituted aryl or alkaryl group, having usefulness as an intermediate for the synthesis of various biologically active compounds. The compound can be prepared by the reaction of an isocyanate compound RNCO, R being the same as above, and 2,3-dihydrofuran, preferably, under pressurization up to 2000 atmospheres or higher.

2 Claims, No Drawings

7-SUBSTITUTED-2-OXA[3.2.0]HEPTAN-6-ONE COMPOUND AND METHOD FOR THE PREPARATION THEREOF

This is a divisional application of Ser. No. 08/396,778, filed Mar. 1, 1995 now U.S. Pat. No. 5,550,230.

BACKGROUND OF THE INVENTION

The present invention relates to a novel β-lactam compound and a method for the preparation thereof. More particularly, the invention relates to a novel β-lactam compound useful as an intermediate in the synthetic preparation of various kinds of organic compounds such as sedatives, herbicides, antibiotics and the like as well as to a method for the preparation thereof in a high yield.

As is known, a β-lactam ring constitutes the principal skeleton in the molecular structure of a large number of antibiotics including penicillin as a typical one to play a core role for the physiological activity of the antibiotic. Accordingly, a great number of β-lactam compounds and methods for the preparation thereof have been heretofore proposed with an object to develop novel antibiotics because development of a novel β-lactam compound having activity as an antibiotic is eagerly desired to solve the problem caused by the appearance of bacterial strains having resistance against conventional antibiotics. On the other hand, β-lactam compounds are highlighted as an intermediate in the synthetic preparation of a polyamide compound owing to the high reactivity of the β-lactam ring with a possibility to give β-amino acid derivatives by the reaction with various compounds having reactivity such as alcohols.

Known prior art methods for the synthetic preparation of such a β-lactam compound include a method in which an isocyanate ester compound is reacted with an alkene. Though advantageous because a β-lactam compound can be obtained in a single-step reaction, this method has a disadvantage that the types of the starting isocyanate ester compound and hence the resultant β-lactam product are under limitations because the method is not applicable with full productivity unless the isocyanate ester compound as one of the starting materials has a strongly electron-attractive group in the molecular structure as in chlorosulfonyl isocyanate and the like.

SUMMARY OF THE INVENTION

The present invention accordingly has an object to provide a novel β-lactam compound not known in the prior art nor described in any literatures by which a possibility can be obtained to synthesize various kinds of β-lactam ring-containing compounds having usefulness as a physiologically active agent as well as an efficient method for the synthetic preparation of such a β-lactam compound.

Thus, the novel β-lactam compound provided by the present invention is a 7-substituted-2-oxa-7-azabicyclo-[3.2.0]heptan-6-one represented by the general formula

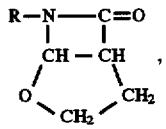
(I)

in which R is a monovalent group selected from the class consisting of alkyl groups, cycloalkyl groups, aryl groups, halogen-substituted aryl groups and alkaryl groups.

The above defined novel β-lactam compound can be synthetically prepared by a very simple method which comprises the step of mixing an isocyanate ester compound represented by the general formula RNCO, in which R has the same meaning as defined above, and 2,3-dihydrofuran to effect an addition reaction between the reactants. The reaction can be promoted, especially when the group denoted by R is a non-halogenated hydrocarbon group, by keeping the reaction mixture under a superatmospheric pressure of 2000 atmospheres or higher.

DETAILED DESCRIPTION OF THE PREFERRED EMBODIMENTS

As is described above, the novel β-lactam compound of the present invention is a 7-substituted-2-oxa-7-azabicyclo-[3.2.0]heptan-6-one represented by the general formula (I) given above and the compound can be prepared merely by mixing a isocyanate ester compound and 2,3-dihydrofuran.

The isocyanate ester compound as one of the above mentioned reactants is represented by the general formula RNCO, in which the group denoted by R is selected from the class consisting of alkyl groups having 1 to 18 carbon atoms such as methyl, ethyl, propyl and butyl groups, cycloalkyl groups such as cyclohexyl group, aryl groups such as phenyl and naphthyl groups, alkaryl groups, i.e. aryl groups substituted by an alkyl group such as methyl, ethyl, propyl and butyl groups and aryl groups substituted by an atom of halogen such as chlorine, bromine and fluorine.

Particular examples suitable for use as the starting isocyanate compound in the synthesis of the novel β-lactam compound include alkyl isocyanates such as methyl isocyanate, ethyl isocyanate, propyl isocyanate, butyl isocyanate, pentyl isocyanate and hexyl isocyanate, cycloalkyl isocyanates such as cyclohexyl isocyanate and cycloheptyl isocyanate, aryl isocyanates such as phenyl isocyanate and naphthyl isocyanate, halogenated phenyl isocyanates such as 2-, 3- and 4-chlorophenyl isocyanates, 2-, 3- and 4-bromophenyl isocyanates and 2-, 3- and 4-fluorophenyl isocyanates and alkylphenyl isocyanates such as 2-, 3- and 4-methylphenyl isocynates and 2-, 3- and 4-ethylphenyl isocynates.

Although the isocyanate ester compound reacts with 2,3-dihydrofuran stoichiometrically in a 1:1 molar ratio, it is preferable that the reaction mixture is formed by mixing the isocyanate ester compound with an excess amount of 2,3-dihydrofuran so that the excess of the latter reactant serves as a reaction medium or diluent. In this case, the amount of 2,3-dihydrofuran is preferably in the range from 1 to 10 moles per mole of the isocyanate ester compound. When an inert organic solvent is used as the reaction medium, however, the amount of 2,3-dihydrofuran can be as small as from 0.8 to 1.2 moles per mole of the isocyanate ester compound. Examples of suitable inert organic solvents include aromatic hydrocarbon compounds such as benzene, toluene and xylene, ethers such as diethyl ether, dipropyl ether and methyl ethyl ether and esters such as ethyl acetate and butyl acetate.

The reaction can proceed even at room temperature but it is preferable to increase the reaction temperature in the range, for example, from 40° to 100° C. although still higher temperatures are undesirable due to the increase in the amount of by-products produced by side reactions. It has been discovered that the reaction can be promoted by increasing the pressure so that the reaction is conducted preferably in a sealed tube or in an autoclave under pressurization of 2000 to 12000 atmospheres. When the reaction conditions including temperature and pressure are adequately selected, the reaction is usually complete within 1 to 50 hours.

The reaction mixture after completion of the reaction can be subjected to a conventional isolation and purification procedure such as dry column chromatography to isolate the desired product. The thus prepared β-lactam compounds are useful as an intermediate for the synthesis of, for example, β-amino acid derivatives, sedative agents having a lactam skeleton in the molecular structure, herbicides having a structure of 2-substituted aminotetrahydrofuran, antibiotics having a molecular structure resembling penicillin and so on.

For example, the β-lactam compound of the invention is first subjected to a ring-opening hydrolysis reaction of the lactam ring into a β-amino acid derivative which can be converted by a dehydrogenation reaction into a 2-amino-3-carboalkoxy-4,5-dihydrofuran derivative having usefulness as a sedative according to the disclosure in Japanese Patent Kokai 49-13163 or can be converted by decarboxylation into a 2-monosubstituted aminotetrahydrofuran compound followed by N-substitution to give a 2-disubstituted aminotetrahydrofuran compound having usefulness as a herbicide according to the disclosure in Japanese Patent Kokai 61-225179.

In the following, examples are given to illustrate the method of the present invention to prepare the novel β-lactam compound and characterization of the product compounds in more detail.

EXAMPLE 1

A mixture consisting of 0.78 g (5.1 mmoles) of 4-chlorophenyl isocyanate and 1.75 g (25 mmoles) of 2,3-dihydrofuran was sealed in a Teflon tube and heated in an autoclave at 100° C. for 20 hours under a pressure of about 7 atmospheres to effect the reaction between the reactants. After completion of the reaction time, the reaction mixture taken out of the autoclave was subjected to dry column chromatography on silica gel using a 2:1 mixture of hexane and ethyl acetate as the developer to obtain 1.03 g of a purified product which could be identified from the identification data shown below to be 7-(4-chlorophenyl)-2-oxa-7-azabicyclo[3.2.0]heptan-6-one which is a compound of the general formula (I) with R being a 4-chlorophenyl group. The above mentioned yield of this product compound corresponds to 93% of the theoretical value.

melting point: 94.5° C.

infrared absorption spectrum: 1748 cm$^{-1}$ (C=O)

mass spectrum (m/z): 223 (M$^+$) ($C_6H_{10}O_2NCl$=223.5)

$^1$H-NMR: (δ, ppm)

1.76–1.95 (m, 1H)

2.23–2.38 (dd, 1H)

3.78–3.98 (m, 2H)

4.22–4.31 (t, 1H)

5.90 (d, 1H)

7.08–7.32 (m, 2H)

$^{13}$C-NMR: (δ, ppm)

165.10, 135.29, 129.41, 129.20, 118.15, 85.85, 67.00, 56.08, 25.33

Elementary analysis: (%)

C H N O calculated for $C_6H_{10}O_2NCl$ 59.07 4.51 6.26 14.31 found 59.06 4.44 6.16 14.51

EXAMPLE 2

The experimental procedure was substantially the same as in Example 1 excepting replacement of the 4-chlorophenyl isocyanate with the same amount of 3-chlorophenyl isocyanate to give 1.02 g of a reaction product which could be identified to be 7-(3-chlorophenyl)-2-oxa-7-azabicyclo [3.2.0]-heptan-6-one which is a compound of the general formula (I) with R being a 3-chlorophenyl group. The yield of the product was 91% of the theoretical value.

infrared absorption spectrum: 1759 cm$^-$(C=O)

mass spectrum (m/z): 223 (M$^+$) ($C_6H_{10}O_2NCl$=223.5).

EXAMPLE 3

The experimental procedure was substantially the same as in Example 1 excepting replacement of 0.78 g of the 4-chlorophenyl isocyanate with 0.77 g (5.0 mmoles) of 2-chlorophenyl isocyanate to give 0.75 g of a reaction product which could be identified to be 7-(2-chlorophenyl)-2-oxa-7-azabicyclo[3.2.0]heptan-6-one which is a compound of the general formula (I) with R being a 2-chlorophenyl group. The yield of the product was 64% of the theoretical value.

infrared absorption spectrum: 1763 cm$^{-1}$ (C=O)

mass spectrum (m/z): 223 (M$^+$) ($C_6H_{10}O_2NCl$=223.5).

EXAMPLE 4

The experimental procedure was substantially the same as in Example 1 excepting replacement of 0.78 g of the 4-chlorophenyl isocyanate with 0.67 g (5.0 mmoles) of 4-methylphenyl isocyanate to give 0.69 g of a reaction product which could be identified to be 7-(4-methylphenyl)-2-oxa-7-azabicyclo[3.2.0]heptan-6-one which is a compound of the general formula (I) with R being a 4-methylphenyl group. The yield of the product was 68% of the theoretical value.

infrared absorption spectrum: 1753 cm$^{-1}$ (C=O)

mass spectrum (m/z): 203 (M$^+$) ($C_{12}H_{13}O_2N$=203).

EXAMPLE 5

The experimental procedure was substantially the same as in Example 1 excepting replacement of 0.78 g of the 4-chlorophenyl isocyanate with 0.84 g (5.0 mmoles) of naphthyl isocyanate to give 0.75 g of a reaction product which could identified to be 7-naphthyl-2-oxa-7-azabicyclo [3.2.0]-heptan-6-one which is a compound of the general formula (I) with R being a naphthyl group. The yield of the product was 63% of the theoretical value.

infrared absorption spectrum: 1755 cm$^{-1}$ (C=O)

mass spectrum (m/z): 239 (M$^+$) ($C_{15}H_{13}O_2N$=239).

EXAMPLE 6

The experimental procedure was substantially the same as in Example 1 excepting replacement of 0.78 g of the 4-chlorophenyl isocyanate with 0.84 g (7.1 mmoles) of phenyl isocyanate to give 1.20 g of a reaction product which could be identified to be 7-phenyl-2-oxa-7-azabicyclo[3.2.0]-heptan-6-one which is a compound of the general formula (I) with R being a phenyl group. The yield of the product was 86% of the theoretical value.

infrared absorption spectrum: 1757 cm$^{-1}$ (C=O)

mass spectrum (m/z): 189 (M$^+$) ($C_{11}H_{11}O_2N$=189),

EXAMPLE 7

A mixture consisting of 0.84 g (7.1 mmoles) of phenyl isocyanate and 1.75 g (25 mmoles) of 2,3-dihydrofuran was sealed in a Teflon tube which was heated in a high-pressure reactor at 40° C. for 20 hours under a pressure of 8000 atmospheres to effect the reaction. After the above mentioned reaction time, the reaction mixture was taken out of the reactor and quantitatively analyzed for the content of the desired product, i.e. 7-phenyl-2-oxa-7-azabicyclo-[3.2.0] heptan-6-one, by the GLC method with hexadecane as an internal standard to find that the content thereof corresponded to 83% of the theoretical yield.

To examine the effect of the pressure for the reaction, the same synthetic procedure as above was repeated except that the pressure was decreased to 4000 atmospheres and 2000 atmospheres to find that the content of the desired product in the reaction mixture after the reaction time corresponded to 70% and 35%, respectively, of the theoretical yield.

For further comparison, the same synthetic procedure as above was repeated under normal pressure instead of pressurization to find that the content of the desired product in the reaction mixture after the reaction time corresponded to only 6% of the theoretical yield.

EXAMPLE 8

The experimental procedure was substantially the same as in Example 1 except that the reaction mixture was prepared from 0.31 g (3.1 mmoles) of butyl isocyanate and 1.05 g (15 mmoles) of 2,3-dihydrofuran and the reaction was performed under a pressure of 8000 atmospheres in A high-pressure reactor to give 0.40 g of a reaction product, after isolation and purification by the dry column chromatography performed in the same manner as in Example 1, which could be identified to be 7-butyl-2-oxa-7-azabicyclo[3.2.0]heptan-6-one which is a compound of the general formula (I) with R being a butyl group. The yield of the product was 77% of the theoretical value.

infrared absorption spectrum: 1759 cm$^{-1}$ (C=O)

mass spectrum (m/z): 169 (M$^+$) (C$_9$H$_{15}$O$_2$N=169).

EXAMPLE 9

The experimental procedure was substantially the same as in Example 8 excepting replacement of 0.31 g of the butyl isocyanate with 0.38 g (3.0 mmoles) of cyclohexyl isocyanate to give 0.40 g of a reaction product which could be identified to be 7-cyclohexyl-2-oxa-7-azabicyclo[3.2.0]-heptan-6-one which is a compound of the general formula (I) with R being a cyclohexyl group. The yield of the product was 68% of the theoretical value.

infrared absorption spectrum: 1755 cm$^{-1}$ (C=O)

mass spectrum (m/z): 195 (M$^+$) (C$_{11}$H$_{17}$O$_2$N=195).

EXAMPLE 10

A Teflon tube containing a mixture of 0.36 g (3.0 mmoles) of phenyl isocyanate, 0.26 g (3.7 mmoles) of 2,3-dihydrofuran and 2 ml of toluene sealed therein was heated at 100° C. for 20 hours under a pressure of 7500 atmospheres in a high-pressure reactor. The reaction mixture after completion of the reaction time was quantitatively analyzed for the content of the desired product 7-phenyl-2-oxa-7-azabicyclo[3.2.0]heptan-6-one by the GLC method with hexadecane as the internal standard to find that the content thereof corresponded to 96% of the theoretical yield.

What is claimed is:

1. A method for the preparation of a β-lactam compound which is a 7-substituted-2-oxa-7-azabicyclo[3.2.0]heptan-6-one represented by the formula

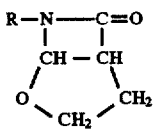

in which R is a monovalent member selected from the group consisting of alkyl, cycloalkyl, aryl, halogen-substituted aryl and alkaryl, which comprises the step of:

reacting a mixture of an isocyanate compound represented by the formula

in which the symbol R has the same meaning as defined above, and 2,3-dihydrofuran.

2. The method for the preparation of a β-lactam compound as claimed in claim 1 in which the mixture of the isocyanate compound and 2,3-dihydrofuran is brought under a pressure of 2000 atmospheres or higher.

* * * * *